(12) United States Patent
Laub et al.

(10) Patent No.: US 12,080,410 B2
(45) Date of Patent: Sep. 3, 2024

(54) SYSTEM AND METHODS OF ADMINISTERING A STATUS CHECK TO A MEDICAL DEVICE

(71) Applicant: Ventis Medical, Inc., Princeton, NJ (US)

(72) Inventors: Glenn W. Laub, Princeton, NJ (US); Taylor R. Laub, Princeton, NJ (US); David G. Laub, Princeton, NJ (US); Giovanni Meier, Madison, CT (US); Steven Jacobson, New York, NY (US); Bob Gorry, New Haven, CT (US)

(73) Assignee: VENTIS MEDICAL, INC., Princeton, NJ (US)

( * ) Notice: Subject to any disclaimer, the term of this patent is extended or adjusted under 35 U.S.C. 154(b) by 0 days.

(21) Appl. No.: 18/348,768

(22) Filed: Jul. 7, 2023

(65) Prior Publication Data

US 2023/0377736 A1    Nov. 23, 2023

Related U.S. Application Data

(63) Continuation of application No. 17/769,438, filed as application No. PCT/US2021/049771 on Sep. 10, 2021, now Pat. No. 11,742,078.

(60) Provisional application No. 63/151,913, filed on Feb. 22, 2021, provisional application No. 63/077,197, filed on Sep. 11, 2020.

(51) Int. Cl.
*G16H 40/40* (2018.01)
*G16H 40/63* (2018.01)

(52) U.S. Cl.
CPC ............. *G16H 40/40* (2018.01); *G16H 40/63* (2018.01)

(58) Field of Classification Search
CPC .............................. G16H 40/40; G16H 40/63
USPC .......................................................... 705/2–3
See application file for complete search history.

(56) References Cited

U.S. PATENT DOCUMENTS

| | | | |
|---|---|---|---|
| 10,449,379 B2 | 10/2019 | Kutek | |
| 2004/0155772 A1* | 8/2004 | Medema | H04W 64/00 340/539.12 |
| 2004/0162586 A1* | 8/2004 | Covey | A61N 1/0472 607/5 |

(Continued)

FOREIGN PATENT DOCUMENTS

| | | |
|---|---|---|
| JP | 2008-136660 A | 6/2008 |
| JP | 2017-508558 A | 3/2017 |

OTHER PUBLICATIONS

English Translation of Notice of Reasons for Refusal for corresponding Japanese Patent Application No. 2023-516475 dated Jul. 31, 2023.

(Continued)

*Primary Examiner* — Michael Tomaszewski
(74) *Attorney, Agent, or Firm* — Morgan, Lewis & Bockius LLP (57) ABSTRACT

A system for administering a status check to a medical device. The system includes a medical device unit comprising a control system, a writing device, and one or more components, the control system configured to transmit to the one or more components a request for status data regarding a status of the one or more components, receive status data from the one or more components, and write, using the writing device, the status data to a transmitting device, the transmitting device configured to store and transmit the status data.

13 Claims, 5 Drawing Sheets

(56) References Cited

U.S. PATENT DOCUMENTS

| | | | | |
|---|---|---|---|---|
| 2012/0116364 A1* | 5/2012 | Houser | ............. | A61B 46/10 |
| | | | | 606/1 |
| 2013/0239038 A1* | 9/2013 | Skidmore | ............. | G16H 40/63 |
| | | | | 715/771 |
| 2015/0031962 A1* | 1/2015 | Chang | ............. | G16H 40/40 |
| | | | | 600/300 |
| 2016/0058996 A1* | 3/2016 | Hoss | ............. | G16H 40/40 |
| | | | | 340/539.13 |
| 2018/0214706 A1* | 8/2018 | Kutek | ............. | A61N 1/3925 |
| 2021/0193305 A1* | 6/2021 | Junker | ............. | G16H 10/40 |
| 2022/0359064 A1* | 11/2022 | Pierson | ............. | G16H 40/40 |

OTHER PUBLICATIONS

English Translation of Notice of Reasons for Refusal for corresponding Japanese Patent Application No. 2023-516475 dated Nov. 17, 2023.
International Search Report and Written Opinion mailed Dec. 10, 2021 for International Patent Application No. PCT/US2021/049771.

* cited by examiner

SYSTEM AND METHODS OF ADMINISTERING A STATUS CHECK TO A MEDICAL DEVICE

CROSS-REFERENCE TO RELATED APPLICATIONS

This application claims priority to U.S. patent application Ser. No. 17/769,438 filed Apr. 15, 2022, which claims priority to International PCT Patent Application No. PCT/US2021/049771, filed Sep. 10, 2021 entitled "System and Methods of Administering a Status Check to a Medical Device", which claims the benefit of U.S. Provisional Application No. 63/077,197 filed Sep. 11, 2020 entitled "Systems and Methods of Administering a Status Check to a Medical Device" and U.S. Provisional Patent Application No. 63/151,913 filed Feb. 22, 2021 entitled "Ventilator System", each of which is incorporated by reference herein in their entirety.

FIELD OF THE INVENTION

The present invention generally relates to a system and method of administering a status check to a medical device and, more particularly, to system and method for administering a status check to a ventilator.

BRIEF SUMMARY OF THE INVENTION

Embodiments of the present invention are directed to a system for administering a status check to a medical device, the system including a medical device unit comprising a control system, a writing device, and one or more components, the control system configured to transmit to the one or more components a request for status data regarding a status of the one or more components, receive status data from the one or more components, and write, using the writing device, the status data to a transmitting device, the transmitting device configured to store and transmit the status data.

In some embodiments, the system further includes an electro-mechanical pneumatic system having a blower and a fan, the electro-mechanical pneumatic system disposed within the medical device unit and coupled to the control system.

In some embodiments, the control system is further configured to display on a user interface the status data via a display screen or a light indicator. The control system may write the status data to the transmitting device based on a periodic basis or an aperiodic basis.

In some embodiments, the control system writes the status data to the transmitting device based on a pre-scheduled basis. The control system may write the status data to the transmitting device in real-time upon receipt of the status data from the one or more components.

In some embodiments, the transmitting device is configured to transmit the status data when the medical device unit is powered off. The transmitting device may be a wireless transmitting device configured to wirelessly receive and transmit the status data. The transmitting device may be a radio frequency identification (RFID) chip.

In some embodiments, the control system is configured to communicate with one or more medical device units in a surrounding area to receive status data associated with the one or more medical device units.

In some embodiments, the system further includes one or more accessories, wherein the control system is configured to receive accessory information associated with the one or more accessories and write the accessory information to the transmitting device.

In some embodiments, the control system is further configured to receive a request for the status data in a non-contact manner.

In some embodiments, the status data comprises device information associated with the medical device unit, the device information including one or more of a serial number, a software version, accessory information, power supply information, date of last status data request, date of last operation, date of manufacture, date of last repair, replaced components, results of previous self-test, usage reports, accessory information, battery information, and battery status.

In some embodiments, the transmitting device automatically transmits the status data on a periodic or aperiodic basis.

In some embodiments, the control system includes a low power controller configured to transmit the request for the status data.

In some embodiments, the medical device further includes a cover configured to protect one or more ports disposed on the medical device, the cover having an open position and a closed position, wherein in a closed position the cover completes a pneumatic pathway.

In some embodiments, the system further includes a beacon configured to provide an indication representative of the status data.

Another embodiment of the present invention may provide a method for administering a status check to a medical device, the method including transmitting, using a control system stored within a medical device unit, a request for status data to one or more components associated with the medical device unit, the status data including information regarding a status of one or more components, wherein the medical device unit is a ventilator, receiving the status data from the one or more components and storing the status data within a memory of the medical device unit, and transmitting the status data to a transmitting device, the transmitting device configured to store the status data and transmit the status data.

In some embodiments, the status data is transmitted to the receiving device without powering on the medical device unit.

Another embodiment of the present invention may provide a method of interrogating a medical device, the method including transmitting, from a reading device, a request for status data describing a status of one or more components associated with a medical device unit, wherein the medical device unit is configured to perform the steps of writing the status data to a transmitting device configured to store the status data, receiving the request for status data from the reading device, and transmitting the status data written to the transmitting device to the reading device, and receiving, from the medical device unit, the status data without powering on the medical device unit.

Another embodiment of the present invention may provide a method of assessing a medical device, the method including receiving an indication of an error from a portable medical device, the error associated with an operation of the portable medical device, the portable medical device having a housing, a user interface, and an electro-mechanical pneumatic system disposed within the housing, wherein the indication is one or more of a visual indication, a text indication, and an audio indication, interacting with the user interface of the portable medical device, the user interface including one or more of a display screen and a speaker, and receiving remediating instructions from the user interface, the remediating instructions associated with remediating the error associated with the operation of the portable medical device.

Another embodiment of the present invention may provide a ventilator including a housing have a top surface, a bottom surface, and a plurality of sidewalls, a user interface disposed on the top surface of the housing, the user interface including one or more of a display screen, an indicator, and a speaker, a pneumatic system disposed within the housing, the pneumatic system including a blower coupled to a motor, a control system disposed within the housing and coupled to the pneumatic system and in communication with a writing device, the controls system configured to transmit a request for status data regarding a status of the pneumatic system, receive from the pneumatic system status data, and write, using the writing device, the status data to a transmitting device, the transmitting device configured to store and transmit the status data.

BRIEF DESCRIPTION OF THE SEVERAL VIEWS OF THE DRAWINGS

The following detailed description of embodiments of the systems and methods of administering a status check to a medical device will be better understood when read in conjunction with the appended drawings of an exemplary embodiment. It should be understood, however, that the invention is not limited to the precise arrangements and instrumentalities shown.

DETAILED DESCRIPTION OF THE EXEMPLARY EMBODIMENTS OF THE INVENTION

Exemplary embodiments of the present invention provide a system and method administering a status check to a medical device. An embodiment of the present invention provides an exemplary system and method as shown in FIGS. 1-5. In use, system 100 may be used for the treatment of patients in a medical setting. For example, system 100 may be a ventilator to assist patients in respiratory distress or acute respiratory failure. System 100 may include medical device unit 102, breathing circuit 200, and patient interface 300. Medical device unit 102 may be configured to provide mechanical ventilation to a patient under respiratory failure through breathing circuit 200. Medical device unit 102 may provide the necessary gas flow or airflow, which may be directed through breathing circuit 200 to patient interface 300, which is coupled to the face of a patient. Medical device unit 102 may include blower 104, control system 106 and power supply 108. Breathing circuit 200 may include tube 202 which may be coupled to medical device unit 102 on at first end 204 and coupled to patient interface 300 at second end 206.

In some embodiments, medical device unit 102 may be a ventilator used to provide assistance to a patient in respiratory distress. Medical device unit 102 may be configured to provide different modes of ventilation to a patient. For example, medical device unit 102 may be configured to provide assist-control ventilation, volume-controlled ventilation, pressure support, pressure-controlled ventilation, pressure regulated volume control, positive end expiatory pressure, synchronized intermittent-mandatory ventilation, and/or manual ventilation. Medical device unit 102 may be used instead of a bag valve device, an emergency transport ventilator, or any other modes or devices for providing ventilation to a patient.

Referring to FIGS. 1-4, medical device unit 102 may include housing 132, blower 104, control system 106, and power supply 108. Housing 132 of medical device unit 102 may house and protect the components disposed within medical device unit 102. Housing 132 may be lightweight to allow for easy portability of medical device unit 102. For example, housing 132 of medical device unit 102 may be made of a lightweight polymer to allow for easy transportation. In some embodiments, housing 132 is comprised of one or more of acrylonitrile butadiene styrene (ABS), polyoxymethylene (POM), Aliphatic Polyamides (PPA) Polycarbonate (PC), Polyphenylsulfone (PPSU), Polyetherimide (PEI), and Polypropylene (PP). Housing 132 may be comprised of a lightweight, but durable material to allow for repeated use in harsh environments, while still providing portability. For example, housing 132 may be comprised of ABS to provide portability and to ensure that the components disposed within housing 132 are secured, protected, and remain undamaged. In some embodiments, housing 132 of medical device unit 102 is substantially rectangular shaped to allow for easy storage. However, housing 132 may be square, circular, triangle, octagonal, or any other shape desired. In some embodiments, housing 132 includes sidewalls 130. In a preferred embodiment, housing 132 includes four sidewalls 130 to define a substantially rectangular shape of medical device unit 102. In some embodiments, housing 132 has rounded corners and beveled edges to allow for a more ergonomic shape.

Figure 2:
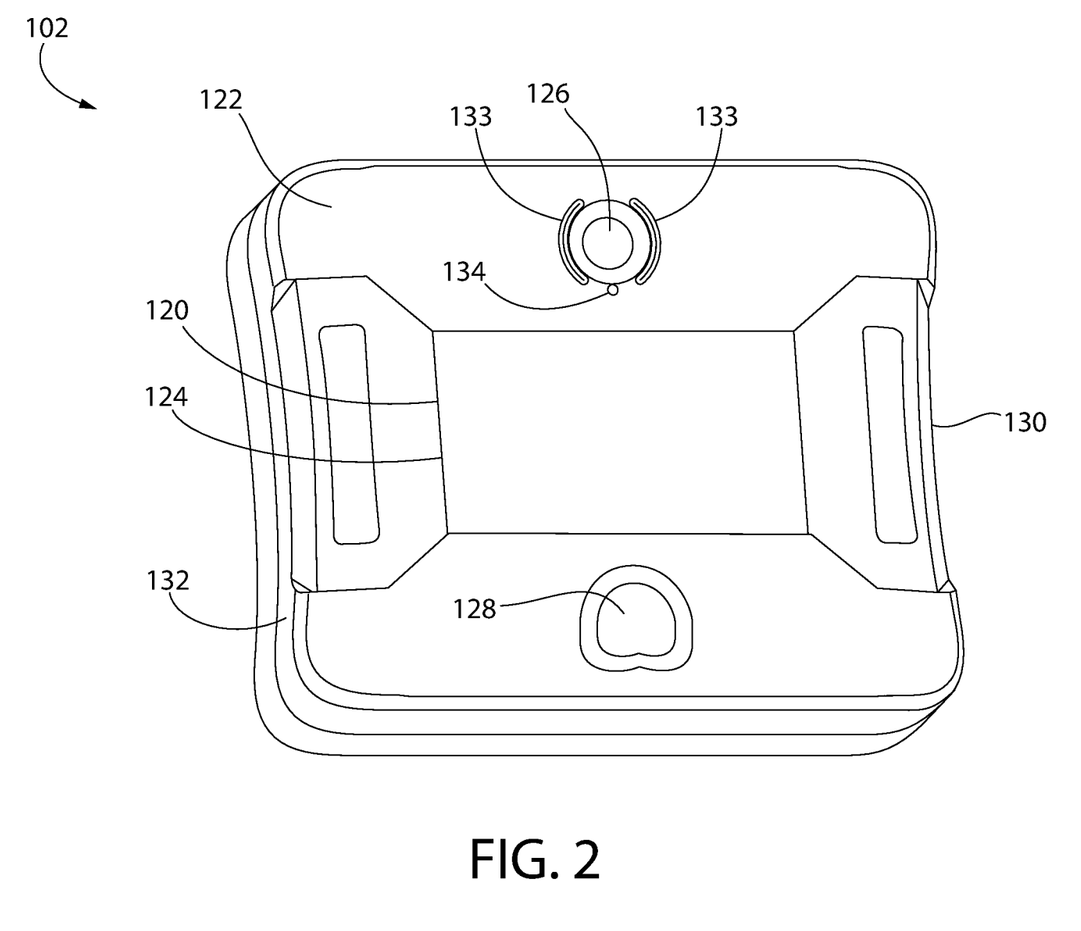
FIG. 2 is a top perspective view of a unit in accordance with an exemplary embodiment of the present invention.
Figure 3:
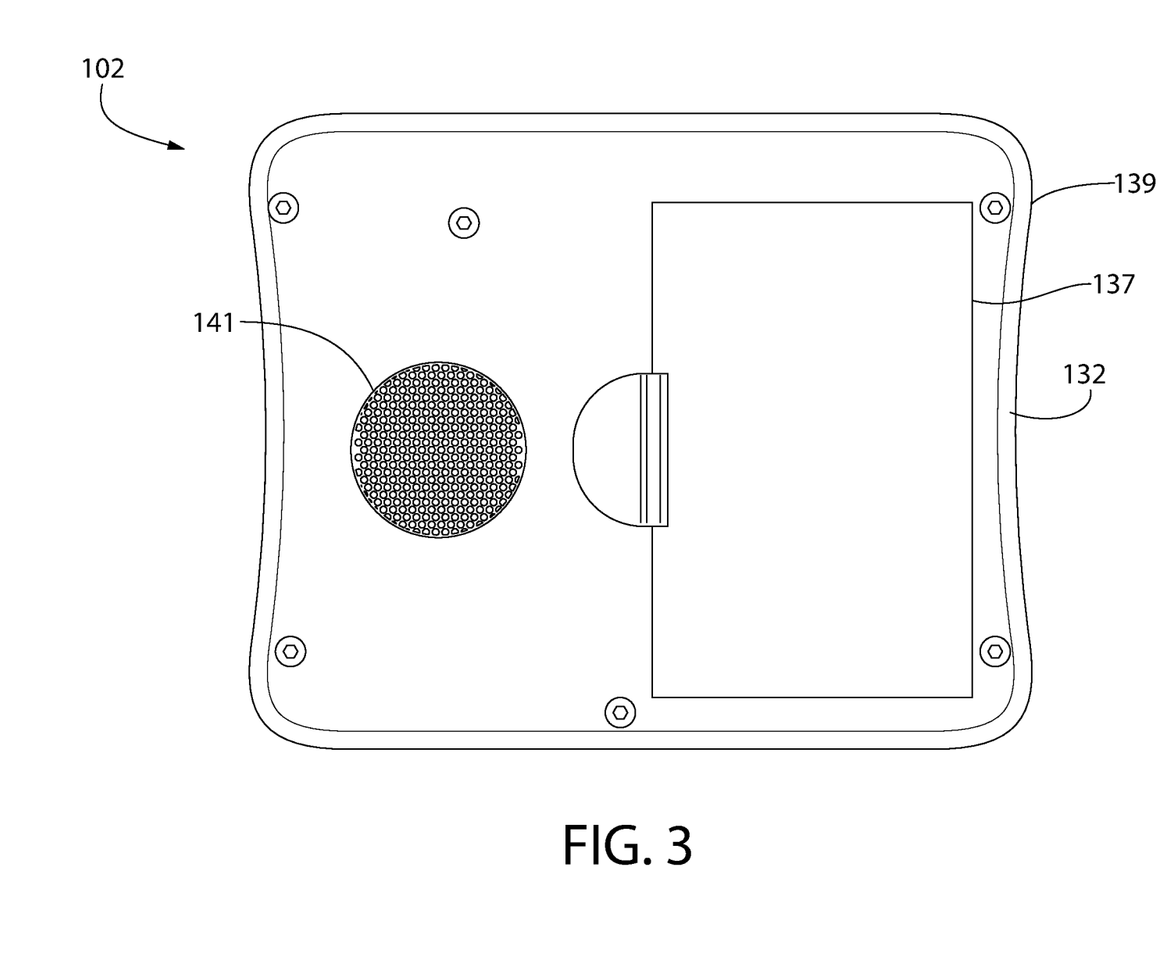
FIG. 3 is a bottom view of the unit in accordance with an exemplary embodiment of the present invention.

Referring to FIGS. 2-3, housing 132 may include top surface 122 and bottom surface 139. In some embodiments, top surface 122 is parallel to bottom surface 139. Top surface 122 may be coupled to bottom surface 139 via sidewalls 130. Housing 132 may include cutout 120 disposed on top surface 122 of housing 132. Cutout 120 may be sized and shaped to receive user interface 124. User interface 124 may be a display device, which may be disposed within cutout 120, and may be configured to receive input from a user. In some embodiments, user interface 124 is a graphical user interface. For example, user interface 124 may be a touch screen configured to receive inputs from a user and transmits the inputs to control system 106. Further, user interface 124 may be used to display information about a patient using medical device unit 102. For example, user interface 124 may display an indication of the respiratory status of a patient coupled to patient interface 300. In some embodiments, user interface 124 may various settings, parameters, and/or functionalities of the components disposed within medical device unit 102. For example, user interface 124 may display the peak inspiratory pressure (PIP), tidal volume (TV), respiratory rate (RR), positive end expiratory pressure (PEEP), inspiratory to expiratory ratio (I:E ratio), ventilation mode, peak flow, and sensitivity. User interface 124 may be coupled to control system 106 and may be configured to control various components of system 100. For example, a user may interact with user interface 124 to change parameters of blower 104. In some embodiments, user interface 124 is configured to display instructions to the user. For example, user interface 124 may provide instructions to a user for correcting an error to medical device unit 102. In some embodiments, user interface 124 is configured to display a video or graphics to a user to instruct them on how to fix or address an error to medical device unit 102.

In some embodiments, a user interacts with user interface 124 to change various modes and/or parameters of medical device unit 102. For example, user interface 124 may provide an option for adjusting the PEEP, the PIP, the tidal volume, the I:E ratio, or other parameters. In some embodiments, medical device unit 102 includes beacon or indicator 134 to provide a status of system 100. Indicator 134 may provide the status of system 100 and/or medical device unit 102. For example, indicator 134 may indicate whether medical device unit 102 is damaged, inoperable, and/or functionally properly. Indicator 134 may be an LED and control system 106 may transmit a status to indicator 134 causing indicator 134 to illuminate a specific color and flash at specific frequency. However, indicator 134 may be a transmitter configured to transmit an outgoing signal. In some embodiments, indicator 134 is configured to continuously transmit an outgoing signal regarding the status of medical device unit 102. For example, indicator 134 may be configured to continuously transmit a signal without be requested to transmit a signal. Indicator 134 may transmit a signal indicating all components of medical device unit 102 are functioning correctly. In some embodiments, indicator 134 continuously transmits a signal until an error occurs, which interrupts the signal transmission resulting in indicator 134 no longer transmitting a signal. A user may check a receiver to determine whether indicator 134 is transmitting a signal and whether an error has occurred based on the transmission ceasing. In other embodiments, indicator 134 is configured to transmit a first signal when medical device unit 102 is functioning correctly without significant errors and is configured to transmit a second signal when an error occurs. The first signal may be different than the second signal. Indicator 134 may transmit a signal wirelessly via radio frequency, WiFi, cellular signal, Bluetooth, near field communication, or any other type of wireless modality.

In some embodiments, indicator 134 provides a status of medical device unit 102 without requiring a user to interact with or power on medical device unit. For example, indicator 134 may be coupled to a power supply separate from power supply 108 and may be configured to illuminate to provide an indication of a status to a user without the user interacting with medical device unit 102. Indicator 134 may transmit a signal to an external receiving device. In some embodiments, indicator 134 transmits a signal regardless of whether an external receiving device is proximate to medical device unit 102 or whether an external receiving device is requesting data from indicator 134. For example, indicator 134 may be configured to transmit a signal regardless of whether a device is listening or whether a device is requesting a signal from indicator 134. In some embodiments, indicator 134 is configured to always be transmitting a signal when medical device unit 102 is functioning correctly or operating normally.

In practice, control system 106 may perform a self-test or status check without user intervention and may cause indicator 134 to illuminate based on the results of the self-test or status check. A user may view medical device unit 102 after the self-test or status check has been performed and may view indicator 134. Upon viewing indicator 134, a user may be able to determine the status of medical device unit 102 and if there are any errors associated with medical device unit 102 without having to interact with medical device unit 102. Interacting with medical device unit 102 may including actuating one or more buttons on medical device unit 102, powering on medical device unit 102, or engaging with user interface 124. In practice, a user may view indicator 134 immediately after the self-test or status check has been performed or may view indicator 134 after a duration of time as elapsed since the self-test or status check has been performed. In some embodiments, control system 106 is configured to transmit a signal to indicator 134 regardless of the power status of medical device unit 102. In other words, indicator 134 may be configured to always receive a signal from control system 106 regardless of the power status of medical device unit 102. This may be due to control system 106 and indicator 134 each having their own power supply separate from power supply 108 or control system 106 and indicator 134 sharing a power supply separate from power supply 108. In some embodiments, indicator 134 has a lower power sensor configured to receive a signal from control system 106 to illuminate based on the status of a performed self-test or status check.

In some embodiments, indicator 134 is configured to flash different colors of light. For example, indicator 134 may flash the color green when medical device unit 102 is operating normally, flash the color red when medical device unit 102 is malfunctioning, or flash the color yellow when medical device unit 102 has an error, but can still function. However, indicator 134 may flash or have a constant illumination. Indicator 134 may be any color desired and may alternate between different colors depending on the status of medical device unit 102. In some embodiments, indicator 134 is coupled to a power supply to ensure that indicator 134 is able to continuously provide an indication for the status of medical device unit 102.

In some embodiments, housing 132 also includes indicator 133. Indicator 133 may be similar to indicator 134. Indicator 133 may also indicate the status of medical device unit 102 and may be used to provide alerts to the user regarding an alarm condition. For example, indicator 133 being green may indicate normal operation of medical device unit 102. However, indicator 133 flashing amber, red, yellow, or orange may indicate a malfunction or error with medical device unit 102. In some embodiments, the degree of flashing of indicator 133 indicates the severity of the error. Indicator 134 may also indicate the battery status associated with power supply 108. For example, indicator 134 being green may indicate that the battery of medical device unit 102 is fully charged. Indicator 134 being other colors, such as red, orange, yellow, amber, and/or flashing may indicate a malfunction or power level of the battery.

Medical device unit 102 may include one or more buttons that control system 100. For example, medical device unit 102 may include buttons 126 and 128, which control the power status and functions of medical device unit 102. In some embodiments, button 126 is a power ON/OFF button to control the power status of medical device unit 102. For example, a user may press button 126 to power on medical device unit 102. Button 128 may be a manual breath button, which delivers a single breath at a predetermined tidal volume to a patient. In some embodiments, button 128 may need to be pressed for a predetermined amount of time before medical device unit 102 delivers a single breath to the patient.

Referring to FIGS. 1-4, medical device unit 102 may include pneumatic system or blower 104, which may include motor 110 and fan 112. Pneumatic system 104 may be an electro-mechanical pneumatic system. Motor 110 may be coupled to fan 112 and motor 110 may be configured to rotate fan 112 to generate air flow. In some embodiments, motor 110 is configured to rotate fan 112 at maximum of 37,500 revolutions per minute (RPM). Fan 112 may rotate to generate airflow that exits blower 104. Motor 110 may be coupled to control system 106, which may control motor 110. In some embodiments, fan 112 is configured to provide a maximum of 1,000 liters per minute (LPM). In some embodiments, fan 112 is configured to rotate at greater than 37,500 RPMs and greater than 1,000 LPMs.

In some embodiments, blower 104 may be disposed within enclosure 114. Enclosure 114 may be sized and shaped to receive blower 104 and may be a unitary piece. For example, enclosure 114 may be comprised of two halves and may be configured to receive blower 104 such that blower 104 is disposed within enclosure 114. Enclosure 114 being made comprised of two halves which surround blower 104 allows for the reduction of components and material needed to manufacture system 100. Blower 104 may include an inflow, which may be disposed within enclosure 114. In some embodiments, the inflow of blower 104 may be the only portion of blower 104 disposed within enclosure 114.

Figure 1:
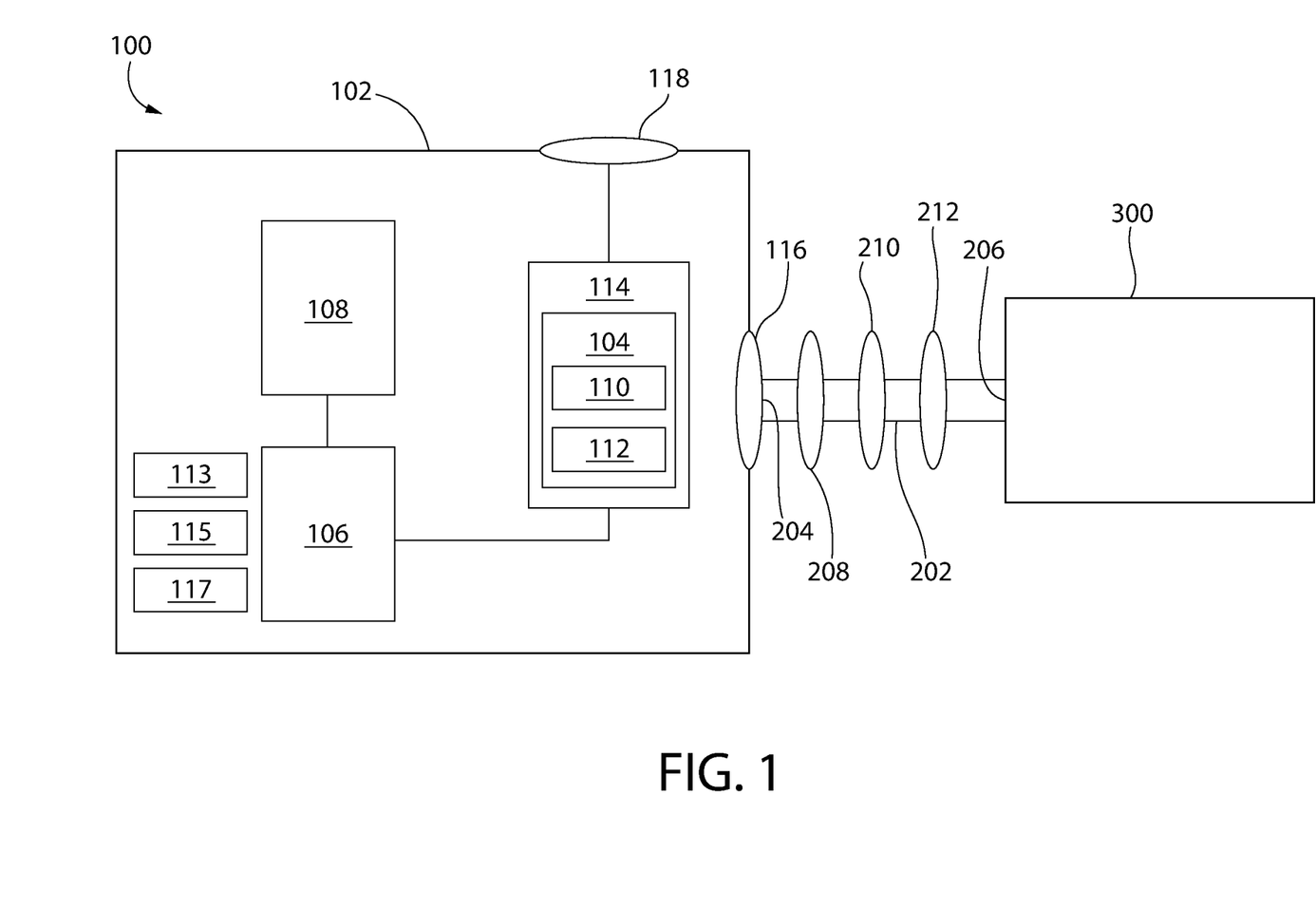
FIG. 1 is a schematic diagram of a system having a unit, breathing circuit, and patient interface in accordance with an exemplary embodiment of the present invention.

Referring to FIG. 1, medical device unit 102 may include control system 106. Control system 106 may be a microcontroller, a peripheral interface controller (PIC), a system on a chip (SoC), or a processor. In some embodiments, control system 106 is a lower power controller. For example, control system 106 may be a lower power controller coupled to a power supply such that control system 106 is configured to run for extended period of time (e.g., several years). Control system 106 may be coupled to one or more components of system 100. In some embodiments, control system 106 is coupled to blower 104 to control motor 110, which controls fan 112. In some embodiments, control system 106 controls the volume of gas delivered to a patient by attenuating the speed of fan 112. For example, controls system 106 may attenuate the power delivered to motor 110, thereby decreasing the speed of fan 112 to reach a target amount of gas delivered to a patient through breathing circuit 200. Control system 106 may include writing device 113, which may be configured to write information to transmitting devices 117, such as radio-frequency identification (RFID) chips/tags. In some embodiments, control system 106 is coupled to power supply 108. However, control system 106 may be coupled to its own power supply.

In some embodiments, writing device 113 is disposed within medical device unit 102. However, writing device 113 may be disposed outside of medical device unit 102 and may be an external device. Writing device 113 may be disposed within, on, or outside of medical device unit 102 and may wirelessly communicate with transmitting device 117. In some embodiments, writing device 113 is configured to wirelessly write information to transmitting devices 117. Writing device 113 may be coupled to control system 106 and may be stored anywhere within medical device unit 102. Writing device 113 may further be coupled to memory 115, which may be coupled to control system 106.

In some embodiments, transmitting device 117 is stored within medical device unit 102 and is communicatively coupled to control system 106. However, transmitting device 117 may be disposed on or near housing 132 of medical device unit 102 and may be configured to wirelessly communicate with control system 106. For example, transmitting device 117 may be coupled to the exterior surface of housing 132 and may wirelessly receive information from control system 106. Transmitting device 117 may be a storage device configured to wirelessly transmit information, such as a wireless transmitting device. For example, transmitting device 117 may include one or more of an RFID chip/tag, a near-field communication chip, a Bluetooth transmitter, a digital barcode, or a WiFi module. In some embodiments, transmitting device 117 only transmits information upon request. However, transmitting device 117 may be configured to transmit information automatically and/or autonomously without intervention by a user or external device. Transmitting device 117 may be configured for low-power consumption. In some embodiments, transmitting device 117 is configured to receive power only from an external source. However, transmitting device 117 may be powered by power supply 108 or its own power supply.

Control system 106 may receive information associated with, for example, the status of system 100 and store the information in memory 115 or directly to transmitting device 117. Writing device 113 may access memory 115 and may write the information stored within memory 115 to transmitting device 117. In some embodiments, memory 115 includes transmitting device 117. Memory 115 may include, for example, random access memory (RAM), a hard disk drive and/or a removable storage drive, such as a floppy disk drive, a magnetic tape drive, an optical disk drive, or a wireless device, such as an RFID tag. Memory 115 may include other similar means for allowing computer programs or other instructions to be loaded into system 100. For example, memory 115 may include a removable memory chip (such as an EPROM, or PROM, or flash memory) and associated socket, and other removable storage units and interfaces which allow software and data to be transferred from a removable storage unit to system 100. In some embodiments, memory 115 is a non-volatile memory. In some embodiments, memory 115 is configured for low-power consumption or configured to receive power only from an external source.

In some embodiment, control system 106 is coupled to power supply 108, which may be configured to provide power to the various components of system 100. For example, control system 106 may be configured to route power from power supply 108 to motor 110 of blower 104. Power supply 108 may be disposed within medical device unit 102. Power supply 108 may include one or more of an internal rechargeable battery, a removable rechargeable battery, and a removable non-rechargeable battery. In some embodiments, control system 106 is coupled to power supply separate from power supply 108.

As shown in FIG. 3, medical device unit 102 may be configured to receive a battery pack via battery storage 137. In some embodiments, a user may place a removable rechargeable battery and/or a removable non-rechargeable battery within battery storage 137. In some embodiments, power supply 108 may be coupled to a power source (not shown) via a power adapter. Power supply 108 may control the voltage and current from a power source to control system 106.

Figure 4:
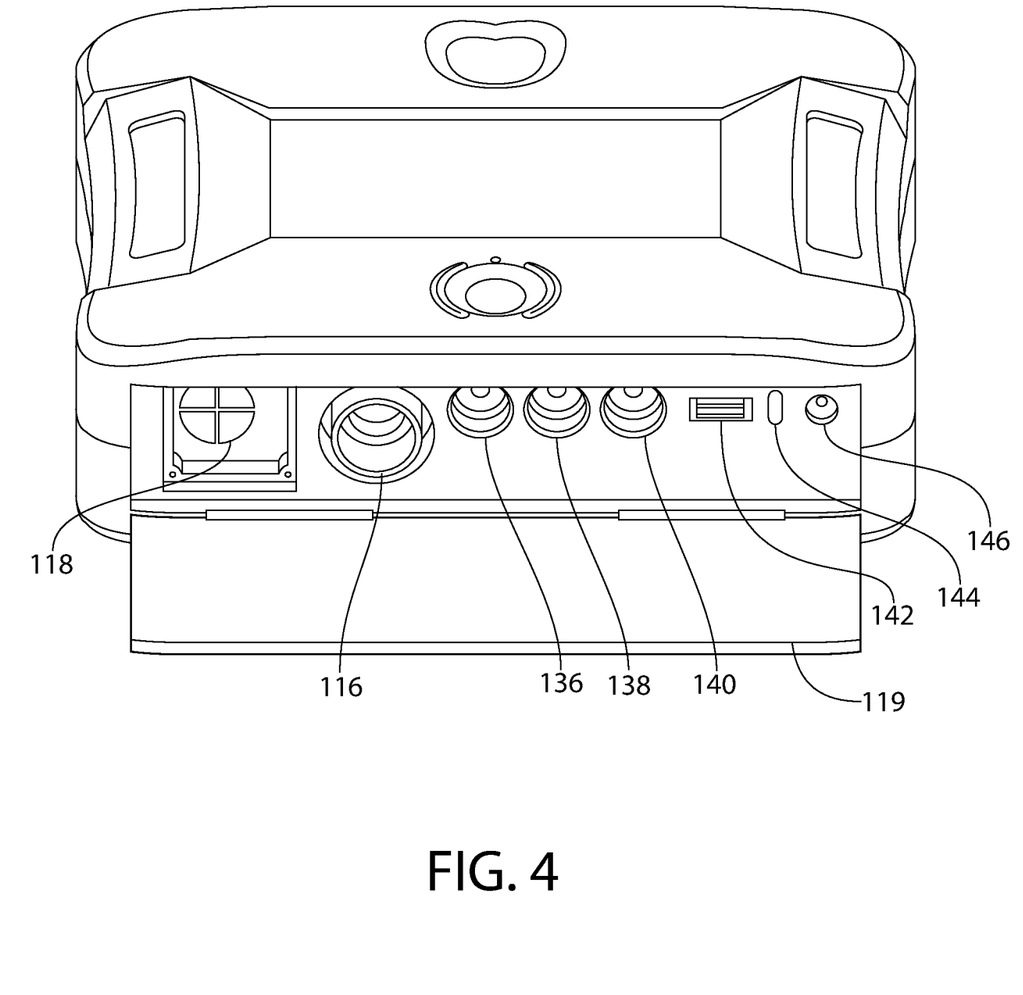
FIG. 4 is a front perspective view of the unit in accordance with an exemplary embodiment of the present invention.

Referring to FIG. 4, in some embodiments, medical device unit 102 may include inlet 118 and outlet 116. Inlet 118 may be disposed on one of sidewalls 130 of housing 132 and allow for air to flow from the external environment (ambient air) or an air source, such as a reservoir of gas ($O_2$), to blower 104. For example, blower 104 may be configured to pull in air from inlet 118 and push the air out through outlet 116. In some embodiments, medical device unit 102 relies on blower 104 to provide air and does not require compressed air to operate. In some embodiments, blower 104 is coupled to outlet 116, which is disposed on an outer periphery of housing 132. For example, outlet 116 may be disposed on sidewall 130 of housing 132. Outlet 116 may be cylindrical in shape and hollow. In some embodiments, outlet 116 couples blower 104 to breathing circuit 200 to patient interface 300. For example, outlet 116 may be configured to allow air to flow from blower 104 of medical device unit 102 through breathing circuit 200 to patient interface 300. In some embodiments, outlet 116 is a valve that may open or close to control the airflow from blower 104 to breathing circuit 200. Outlet 116 may be controlled by air pressure or by control system 106.

Referring to FIG. 1, system 100 may include breathing circuit 200. Breathing circuit 200 may be coupled to medical device unit 102. For example, breathing circuit 200 may be coupled to outlet 116. In some embodiments, breathing circuit 200 may be disposed between medical device unit 102 and patient interface 300. Breathing circuit 200 may be configured to receive air from medical device unit 102. Breathing circuit 200 may include tube 202, exhale valve 208, flow sensor 210, and patient filter 212. Tube 202 may include first end 204 and second end 206. First end 204 may be coupled to medical device unit 102 and second end 206 may be coupled to patient interface 300. In some embodiments, tube 202 is a cylindrical lumen configured to allow airflow from medical device unit 102 to patient interface 300. Tube 202 may be configured to include exhale valve 208, flow sensor 210, and patient filter 212. Exhale valve 208 disposed on or within tube 202 and may be configured to open on exhalation of the patient using system 100 to allow air to flow out of the patient. Exhale valve 208 may be closed during inhalation such that air does not exist system 100, thereby increasing efficiency. For example, exhale valve 208 may be closed during inhalation to ensure that the proper amount and flow of air reaches patient interface 300.

In some embodiments, exhale valve 208 is controlled by control system 106 to control the exhalation of the patient. In another embodiment, exhale valve 208 is controlled based on the exhalation of the patient. In yet another embodiment, exhale valve is controlled by both control system 106 and the exhalation of the patient. Exhale valve 208 may be configured to allow for a specific respiration rate, but may be opened by the exhalation of the patient as well. For example, for a respiration rate of 12 (one breathe ever five seconds), exhale valve 208 may open ever five seconds and may also open more than every five seconds if the patient is breathing at different rate.

In some embodiments, breathing circuit 200 includes flow sensor 210, which may be disposed on or within tube 202. Flow sensor 210 may be configured to sense the flow of air within breathing circuit 200. For example, flow sensor 210 may detect the rate and amount of air flowing through tube 202. In some embodiment, flow sensor 210 is coupled to control system 106 to provide feedback to system 100. For example, flow sensor 210 may provide information to control system 106, which may change the parameters of blower 104 based on the information.

Breathing circuit 200 may further include patient filter 212, which may be disposed proximate second end 206 of tube 202. For example, patient filter 212 may be disposed on or within tube 202 proximate second end 206 and adjacent to patient interface 300. Patient filter 212 may be configured to filter out particles within air. For example, patient filter 212 may filter out particles and airborne viruses to protect the patient using system 100.

Referring to FIG. 1, system 100 may include patient interface 300. Patient interface 300 may be a device that is secured to the face of a patient. For example, patient interface 300 may be a bag valve mask, respirator, or an endotracheal (ET) tube used for intubation.

Referring to FIG. 4, medical device unit 102 may further included various inputs for coupling medical device unit 102 to other components of system 100. In addition to inlet 118 and outlet 116, medical device unit 102 may include control line port 136, pressure line port 138, differential pressure tube port 140, flow sensor port 142, data communication port 144, and power port 146. Control line port 136 may be used to couple exhale valve 208 and medical device unit 102. For example, exhale valve 208 may be coupled to medical device unit 102 at control line port 136 such that medical device unit 102 can control the opening and closing of exhale valve 208. Pressure line port 138 and differential pressure tube port 140 may be used to couple one or more pressure sensors to medical device unit 102. Flow sensor port 142 may be used to couple flow sensor 210 to medical device unit 102. For example, flow sensor 210 may be coupled to medical device unit 102 at flow sensor port 142 such that medical device unit 102 can receive information from flow sensor 210. Data communication port 144 may be used to couple medical device unit 102 to an electronic device such as a computer system, a mobile device, a server, etc. Power port 146 may be used to couple medical device unit 102 to a power source. For example, power port 146 may be configured to couple power supply 108 to a power source to provide power to medical device unit 102 through power supply 108.

Medical device unit 102 may include port plate 119. Port plate 119 may a portion of housing 132 that protects one or more of inlet 118, outlet 116, control line port 136, pressure line port 138, differential pressure tube port 140, flow sensor port 142, data communication port 144, and power port 146. Port plate 119 may be configured to prevent debris from entering the ports of medical device unit 102. In some embodiments, port plate 119 includes one or more filters to filter air/gas entering through various inlets of medical device unit 102. Port plate 119 may be hingedly coupled to housing 132. In some embodiments, port plate 119 is a separate component from housing 132 and may be slidably received by housing 132 adjacent to the ports of medical device unit 102. For example, port plate 119 may be molded to housing 132 and may be manufactured via injection molding.

Inlet 118 may include cover or door 121 disposed over inlet 118. Cover 121 may be configured to allow inlet 118 to be connected to air/gas source, such as an oxygen source. Inlet 118 may also include cover 121 to prevent connection of the wrong connector to inlet 118. For example, inlet 118 may include a specialized cover configured to allow only for reservoirs of only certain gases or fluids to flow into inlet 118. In some embodiments, cover 121 may prevent inadvertent connection of breathing circuit 200 to the wrong connection. In some embodiments, a user would have to actively remove cover 121 from inlet 118 to allow connection of an air/gas source to inlet 118. In some embodiments, cover 121 may be coupled to port plate 119. For example, cover 121 may be hingedly coupled to port plate 119 to allow for covering of inlet 118. In some embodiments, cover 121 may allow ambient air to flow into inlet 118 without removing cover 121 from inlet 118. In some embodiments, cover 121 may have special markings to indicate which sources of air/gas can be coupled to inlet 118. In some embodiments, a special tool is required to remove cover 121 from inlet 118 to prevent inadvertent connection to inlet 118. In some embodiments, cover 121 includes a sensor to only allow removal from inlet 118 when certain gases are detected. Cover 121 may also be configured to prevent debris from entering inlet 118.

In some embodiments, port plate 119 may include a testing cap configured to allow for the testing of airflow and blower 104 of medical device unit 102. The testing cap may be configured to disposed over port plate 119 and allow air coming from outlet 116 of fan 112 to flow through the testing cap into a pressure sensor disposed on port plate 119 or the testing cap. For example, the testing cap may include a recess that allows air to flow form outlet 116 to the pressure sensor to determine the pressure of air provided by blower 104. The recess of the testing cap may allow for air to be channeled from outlet 116 to the pressure sensor, which may be disposed on port plate 119. For example, the testing cap may allow for testing of blower 104 when medical device unit 102 is in storage. The testing cap may be configured to ensure the integrity of pressure sensors of medical device unit 102 in addition to providing additional protection to port plate 119 and outlet 116. In some embodiments, the recess of testing cap may allow air to flow from outlet 116 to other sensors disposed on port plate 119 and/or within the testing cap. The testing cap may be hingedly coupled to port plate 119 or housing 132 and may be configured to be completely removable from medical device unit 102.

Figure 5:
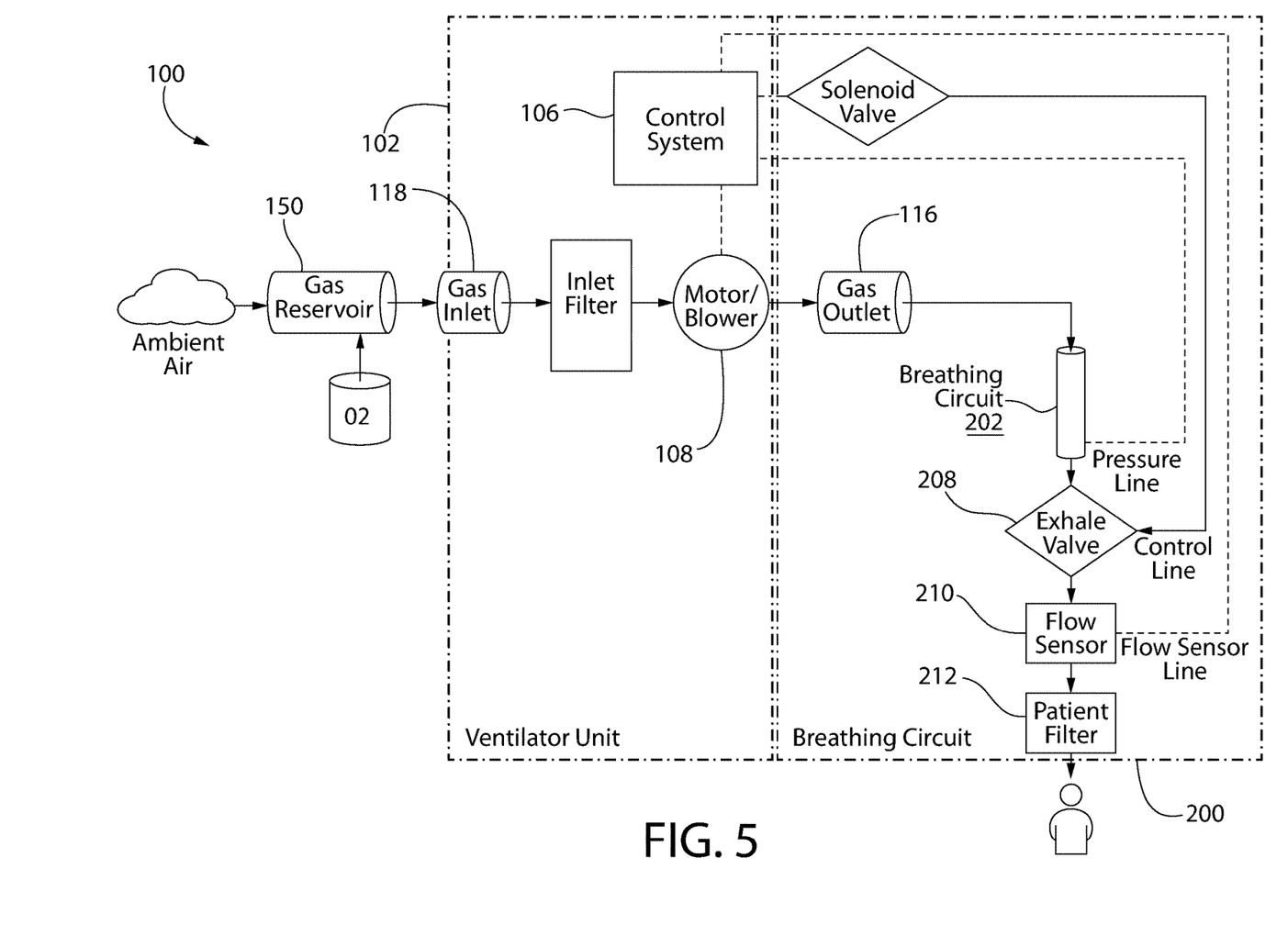
FIG. 5 is a schematic diagram of a system having a unit, breathing circuit, and patient interface in accordance with an exemplary embodiment of the present invention.

Referring to FIG. 5, ambient air and oxygen may both enter gas reservoir 150 and mix together. Gas from gas reservoir 150 may enter medical device unit 102 through inlet 118 to prevent external debris from entering medical device unit 102. The gas is then channeled through an air pathway housed in medical device unit 102, and into breathing circuit 200 through outlet 116. e.

In some embodiments, system 100 may be configured to administer a status check or a self-test to ensure that all components are working properly and that there are not any malfunctions. In some embodiments, control system 106 is configured to test the various components of system 100 to determine the functional status of, for example, blower 104, power supply 108, writing device 113, memory 115, transmitting device 117, and control system 106, in addition to reporting the operational status of system 100. For example, control system 106 may be configured to receive information from memory 115 regarding any corrupted cores, from blower 104 regarding an occlusion of fan 112, from outlet 116 or inlet 118 regarding occlusions, from power supply 108 regarding improper voltages, or any other information necessary to ensure that medical device unit 102 is functioning properly. In some embodiment, control system 106 automatically receives information from various components of system 100 on a periodic or aperiodic basis. For example, control system 106 may receive information for some or all of the components of medical device unit 102 without receiving a request from a user or other device.

In some embodiments, medical device unit 102 of system 100 is configured to administer a status check, store the results of the status check, and then power down. In some embodiments, medical device unit 102 is configured to perform a self-test while medical device unit 102 is in storage or otherwise not in active use (e.g. in a powered down state). The results of the status check may be stored on memory 115, which may be configured to transmit the results without receiving power from medical device unit 102. For example, medical device unit 102 may power on, administer a status check, store the results of the status check on transmitting device 117 and/or memory 115, and then power down. Transmitting device 117 may be configured to transmit the results only when interrogated by an external source. The external source may be a receiving or reading device that provides power to transmitting device 117 enabling transmitting device 117 to transmit the results. This allows medical device unit 102 to conserve power as it does not need to power on to transmit the results of the status check and enables medical device unit 102 to provide results at any time upon interrogation by a user. However, transmitting device 117 may be configured to automatically transmit results on a periodic or aperiodic basis. For example, transmitting device 117 may automatically transmit results without user intervention.

Control system 106 may receive status data regarding the functional status of system 100 and store the status data with memory 115. Status data may be any information describing the functionality and operation of any component of system 100. Writing device 113 may access the status data stored within memory 115 to write the status data to transmitting device 117 stored within medical device unit 102. A user may wirelessly access the status data from transmitting device 117 without requiring medical device unit 102 to power on. This allows medical device unit 102 to be able to transmit status data wirelessly and without powering on, thereby reducing power consumption. For example, a user may interrogate transmitting device 117 and receive the status data while medical device unit 102 is powered off. A user may interrogate transmitting device 117 using a receiving or reading device. In some embodiments, the receiving or reading device may be configured to provide power to transmitting device 117, allowing it to transmit the status data without requiring medical device unit 102 to power on. In some embodiments, medical device unit 102 does not provide power to transmitting device 117. In some embodiments, transmitting device 117 may transmit status data without requiring a user to physically contact medical device unit 102. For example, transmitting device 117 may only transmit status data upon request from an external source, such as a reading or receiving device. However, transmitting device 117 may be configured to autonomously and automatically transmit status data on a periodic or aperiodic basis. In some embodiments, status data may include one or more of the following a serial number, a software version, accessory information, power supply information, date of last status data request, date of last operation, date of manufacture, date of last repair, replaced components, results of prior status checks, usage reports, accessory information, battery information, and battery status.

Control system 106 may automatically test medical device unit 102 on a periodic, scheduled, or a-periodic basis. For example, control system 106 may power on medical device unit 102 and test all the components of medical device unit 102 on a periodic basis such as, for example, every month, every 3 months, or every 6 months. In some embodiments, a user may schedule specific dates for control system 106 to power on medical device unit 102 and test all the components of medical device unit 102. In another embodiment, control system 106 may power on medical device unit 102 and test all the components of medical device unit 102 on an aperiodic basis. For example, tests may need to run more frequently the longer medical device unit 102 is in storage. In some embodiments, control system 106 tests medical device unit 102 without user intervention.

In some embodiments, control system 106 is configured to autonomously power on medical device unit 102 to perform a self-test or status check. For example, control system 106 may be configured to periodically or aperiodically wake medical device unit 102 to perform a self-test or status check. In some embodiments, control system 106 performs a self-test or status check in a "silent mode" such that a user is unable to notice that a self-test or status check is being performed. For example, control system 106 may perform a self-test or status check without turning on user interface 124 or indicators 133, 134 and without user intervention. In some embodiments, a user requests control system 106 to perform a self-test or status check by interacting with user interface 124 or engaging with/actuating button 126. For example, a user may actuate button 126 for approximately 5 seconds to initiate a self-test or status check on medical device unit 102. However, a user may actuate button 126 for 3 seconds, 4, seconds, 6 seconds, or greater than 6 seconds to initiate a self-test or status check.

In some embodiments, control system 106 causes activation of indicators 133, 134, user interface 124 or speaker 141 to indicate that medical device unit 102 is performing a self-test or status check. For example, user interface 124 may illuminate with a message indicating that a self-test or status check is being performed or speaker 141 may produce an audio output to indicate to the user that a self-test or status check is being performed.

In some embodiments, medical device unit 102 is configured to provide instructions on fixing an error. For example, control system 106 may request a self-test or status check on one or more components and may receive an error. In response to the received error, control system 106 may cause user interface 124 and/or speaker 141 to provide instructions to a user. For example, if control system 106 receives an error from one or components, such as blower 104, user interface 124 may display graphics and/or a video instructing a user how to fix the error associated with blower 104. In some embodiments, medical device unit 102 provides step-by-step instructions to a user via user interface 124 or a microphone such that the user progresses through the instructions at their own pace. For example, a user may interact with user interface 124 to progress through step-by-step instructions or may use their voice to instruct medical device unit 102 to skip to the next instructions or repeat instructions for a specific step.

In some embodiments, control system 106 detects an error while medical device unit 102 is in use. For example, an error may occur resulting in medical device unit 102 not functioning correctly while be used with a patient. Control system 106 may detect the error while medical device unit 102 is in use and my provide instructions in real-time to a user to correct the error to allow medical device unit 102 to return to functioning correctly. In some embodiments, control system 106 causes speaker 141 provide audio instructions to the user to fix an error. Speaker 141 may be configured to correspond to graphics and/or videos presented by user interface 124. In some embodiments, user interface 124 is configured to receive inputs from a user to advance or repeat instructions associated with fixing an error.

In some embodiments, control system 106 is configured to transmit text, audio, images, graphics, and/or video regarding fixing an error to an electronic device associated with the user. Control system 106 may be configured to provide instructions for fixing an error while medical device unit 102 is powered on. In practice, control system 106, which may be coupled to a power supply separate from power supply 108, may receive an error from one or more components while medical device unit 102 is powered off. Upon powering on medical device unit 102, control system 106 may cause user interface 124 and/or speaker 141 to provide instructions to a user to fix an error. However, control system 106 may provide instructions to user while medical device unit 102 is in use. In some embodiments, control system 106 receives an error while medical device unit 102 is in use and provides instructions in real time. Control system 106 may receive an error without performing a status check or self-test. For example, during use of medical device unit 102, an error may occur within breathing circuit 200 or patient interface 300. Control system 106 may detect that an error has occurred and may provide instructions to a user via user interface 124 and/or speaker 141 on how to address and correct the error in real-time.

In some embodiments, control system 106 is configured to provide instructions to a user regarding the appropriate therapy or the optimal treatment for a patient. For example, user interface 124 may provide audio, video, graphics, and/or text to a user recommending services and treatments to provide to a patient. In use, various parameters (e.g., PIP, TV, RR, PEEP, I:E ratio, ventilation mode, flow rate) of medical device unit 102 may need to be adjusted by a user when medical device unit 102 is being used for treating a patient. Control system 106 may instruct user interface 124 to provide instructions to a user for adjusting these parameters. In some embodiments, control system 106 provides instructions to a user via user interface 124 based on the current treatment that medical device unit 102 is providing to a patient. For example, medical device unit 102 may be a ventilator providing oxygen to a patient at a specific tidal volume and user interface 124 may provide instructions to a user to vary the tidal volume based on information control system 106 receives from various sensors or components of medical device unit 102.

In practice, multiple medical device units 102 may be stockpiled or placed in storage for a long period of time prior to use and thus may require multiple tests to ensure that medical device unit 102 is functioning properly prior to use. In practice, previous medical devices require physical intervention (e.g. opening device, turning device on, etc.) to determine if the device is functioning properly. This is an inefficient use of resources and also depletes the devices power supply. In some embodiments, medical device unit 102 automatically powers on and runs tests of the various components stored within medical device unit 102 to generate status data. Control system 106 of medical device unit 102 may store the status data within memory 115. Writing device 113 may access the status data from memory 115. In some embodiments, control system 106 sends the status data directly to writing device 113. Writing device 113 may write the status data to transmitting device 117, such as an RFID tag, which stores the status data. After writing device 113 writes the status data to transmitting device 117, medical device unit 102 may shut off to conserve power. A user may retrieve the status data by using a receiving or reading device, such as an RFID reader, to wirelessly receive status data while medical device unit 102 is powered off.

In some embodiments, medical device unit 102 may only transmit the status data when requested by a user. For example, control system 106 may receive the status data and writing device 113 may receive the status data from control system 106 and/or memory 115. Writing device 113 may write the status data to transmitting device 117, which may store the status data. Transmitting device 117 may only transmit the status data when requested by a user, such as by a user placing a receiving device adjacent to medical device unit 102 or by the user interacting with medical device unit 102 via user interface 124 or buttons 126, 128. However, transmitting device 117 may be configured to autonomously transmit status data without user intervention. For example, transmitting device 117 may detect that a receiving device is located proximate to medical device unit 102 and may automatically and autonomously transmit status data. In some embodiments, transmitting device 117 is configured to autonomously and automatically transmit status data on a periodic or aperiodic basis to receiving device located proximate or remote to medical device unit 102.

In some embodiments, control system 106 receives information from accessories associated with medical device unit 102. For example, the accessories may each include one or more wireless transmitting devices, disposed within or on them, configured to transmit information to control system 106 when interrogated. Medical device unit 102 may include one or more accessories that each may store information to their respective wireless transmitting devices. The wireless transmitting devices associated with each of the accessories may store information about the accessory such as the product type, expiration, model number, serial number, modification, last test, last use, etc. In some embodiments, control system 106 may interrogate the wireless transmitting devices to receive accessory information about the accessories and store that accessory information within memory 115. Control system 106 may be configured to interrogate all accessories proximate to medical device unit 102. For example, control system 106 may interrogate all accessories in predetermined radius to ensure that medical device unit 102 has all the accessories it requires to function. Writing device 113 of medical device unit 102 may write the accessory information about the accessories to transmitting device 117, which may store the accessory information along with the status data. In some embodiments, control system 106 is configured to interrogate any accessory or device within a predetermined proximity and/or radius and write any information received to transmitting device 117 and/or memory 115.

In some embodiments, medical device unit 102 is configured to create a mesh network with surrounding medical device units, allowing for the transmitting and receiving of status data associated with multiple medical device units. Medical device unit 102 may be configured to interrogate one or more medical device units within close proximity or a predetermined radius. Each medical device unit may be configured to interrogate adjacent medical device units and store information relating to the status data of the medical device units in close proximity such that each medical device unit includes status data of all medical device units in a surrounding area. For example, medical device unit 102 may interrogate and write status data related to all medical device units in a surrounding area to transmitting device 117 and/or memory 115. This allows a user to only have to interrogate a single medical device unit to obtain information from all medical device units in a surrounding area. The surrounding area may be a radius of at least 1 foot, at least 2 feet, at least 3 feet, at least 4 feet, at least 5 feet, at least 10 feet, or at least 25 feet. In some embodiments, medical device unit 102 may interrogate surrounding medical device units to determine the status of accessories associated with the surrounding medical device units. This allows a user to determine which medical device units and/or accessories need attention by interrogating only medical device unit 102.

In some embodiments, the mesh network created by medical device unit 102 and the surrounding medical device units allows control system 106 to map the location of surrounding medical device units along with status data associated with each medical device unit. This allows for a user to interrogate medical device unit 102 and obtain status data for all surrounding medical device units, in addition to determining the location of the surrounding medical device units. Determining the location of the surrounding medical device units, allows a user to easily determine, based on the status data which medical device unit is not functioning properly and allows the user to easily find and replace the malfunctioning medical device unit. In some embodiments, medical device unit 102 is configured to transmit a map of the locations of the surrounding medical device units to the user when requested.

In some embodiments, medical device unit 102 may include a wireless network module, such as a WiFi chip/card, configured to communicate with control system 106 and one or more external devices. The one or more external devices may include writing device 113, transmitting device 117, a server, a computer, a mobile device, or an external transmitter. The wireless network module may receive a signal from an external device causing medical device unit 102 to power on and administer a status check. The status data resulting from the status check may be stored within memory 115 and/or may be wirelessly transmitted to writing device 113, which may be disposed outside of medical device unit 102. Writing device 113 may then write status data to transmitting device 117, which may be stored within, on, or external to housing 132 of medical device unit 102. In some embodiments, writing device 113 and transmitting device 117 are each disposed proximate to medical device unit 102. In alternative embodiments, writing device 113 and transmitting device 117 are each disposed remote to medical device unit 102.

In some embodiments, medical device unit 102 may provide status data via additional methods. In some embodiments, indicator 133 on medical device unit 102 may provide the status of medical device unit 102. For example, indicator 133 may be an LED indicator or status light that may display a green light if there are no malfunctions or may display a red light if there are malfunctions. When a red light is displayed, indicating a malfunction of medical device unit 102, a user may retrieve the status data from transmitting device 117 to receive detailed results of the test to address the malfunction. In some embodiment, a receiving device and/or writing device 113 is disposed adjacent to medical device unit 102 to constantly receive status data from or write data to transmitting device 117 whenever medical device unit 102 runs tests of the various components stored within medical device unit 102. For example, whenever a test of medical device unit 102 is run, control system 106 and/or memory 115 may provide transmitting device 117 with the status data. Transmitting device 117 may transmit the status data to the receiving device upon receipt of the status data. The receiving device may alert a user when there are any malfunctions contained within the status data or may transmit the status data to a central server or database for a user to access. This may allow for the monitoring of multiple medical device units 102 in storage without having a user having to periodically check on the status of each medical device unit 102 in storage. Further, this allows for real-time broadcasting of status data from medical device unit 102.

In some embodiments, medical device unit 102 may include speaker 141, additional lights, and/or additional display screens. Medical device unit 102 may be configured to alert a user via one or more of user interface 124, indicators 133, 134, user interface 124, display screens, or other modes of alerting a user. For example, medical device unit 102 may provide an alert, warning or message to a user by text, audio, or visual indicators. Medical device unit 102 may provide alerts for one or more of electricity supply failure, medical device unit 102 being switched off while in a specific mode, inspiratory and PEEP pressure exceeding a predetermined threshold values, or inspiratory and PEEP pressure going below a do not achieve minimum threshold values, tidal volume or respiratory rate (RR) not being achieved or being exceeded, medical device unit 102 being disconnected from power, obstruction of blower 104, or apnea. As discussed herein, medical device unit 102 may be configured to provide instructions to a user on how to fix an error detected by control system 106 via one or more of user interface 124, speaker 141, or an electronic device associated with a user.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A method of assessing a medical device, the method comprising:
   transmitting, using a control system disposed within a portable medical device unit, a request for status data to one or more components associated with the portable medical device unit, the status data including information regarding a status of one or more components;
   receiving, using the control system, the status data from the one or more components and storing the status data within a memory of the portable medical device unit;
   in response to receiving the status data, determining an error associated with the one or more components based on the status data, the error associated with an operation of the portable medical device, the portable medical device having a housing, a user interface, and a pneumatic system disposed within the housing;
   providing, using the control system, an indication of the error, wherein the indication is one or more of a visual indication, a text indication, and an audio indication;
   generating, using the control system, remediating instructions associated with remediating the error associated with the operation of the portable medical device; and
   displaying, using the user interface, the remediating instructions.

2. The method of claim 1 further comprising:
   transmitting the status data to a transmitting device, the transmitting device configured to store the status data and transmit the status data.

3. The method of claim 1, wherein the pneumatic system includes a blower and a fan, and is disposed within the portable medical device unit and coupled to the control system.

4. The method of claim 1, wherein display on a user interface the status data via a display screen or a light indicator.

5. The method of claim 1, wherein the control system receives the status data when the medical device unit is powered off.

6. The method of claim 1, wherein the control system is configured to receive accessory information associated with one or more accessories and determine an accessory error associated with the one or more accessories.

7. The method of claim 1 further comprising:
   receiving a data request for the status data in a non-contact manner.

8. The method of claim 1, wherein the status data comprises device information associated with the medical device unit, the device information including one or more of a serial number, a software version, accessory information, power supply information, date of last status data request, date of last operation, date of manufacture, date of last repair, replaced components, results of previous self-test, usage reports, accessory information, battery information, and battery status.

9. The method of claim 1, wherein the portable medical device unit includes a beacon configured to provide a status indication representative of status data.

10. The method of claim 1, wherein the control system receives the status data from the one or more components without powering on the medical device unit.

11. The method of claim 1, wherein the portable medical device unit is a ventilator.

12. The method of claim 1, wherein the pneumatic system is an electro-mechanical pneumatic system and includes a blower coupled to a motor.

13. The method of claim 1, wherein the user interface is disposed on a top surface of the housing, the user interface including one or more of a display screen, an indicator, and a speaker.

* * * * *